United States Patent [19]

Aita et al.

[11] Patent Number: 5,093,877

[45] Date of Patent: Mar. 3, 1992

[54] OPTICAL FIBER LASING APPARATUS LENS

[75] Inventors: Michael Aita; Robert F. Kotmel, both of Sunnyvale; Gene Samson, Milpitas, all of Calif.

[73] Assignee: Advanced Cardiovascular Ssytems, Santa Clara, Calif.

[21] Appl. No.: 605,658

[22] Filed: Oct. 30, 1990

[51] Int. Cl.⁵ .............................................. G02B 6/32
[52] U.S. Cl. ...................................... 385/34; 385/33; 606/15
[58] Field of Search ............................ 350/96.18, 432; 128/398; 606/15, 16, 17; 385/33, 34, 35

[56] References Cited

U.S. PATENT DOCUMENTS

| | | | |
|---|---|---|---|
| 4,273,109 | 6/1981 | Enderby | 606/16 |
| 4,842,390 | 6/1989 | Sottini et al. | 606/17 |
| 4,917,084 | 3/1990 | Sinofsky | 128/398 |

*Primary Examiner*—James W. Davie
*Attorney, Agent, or Firm*—McCubbrey, Bartels, Meyer & Ward

[57] ABSTRACT

An optical fiber lasing apparatus includes an optical fiber which terminates in a lens having a convex lens side at its forward end, and having an extended barrel portion secured to the distal portion of the optical fiber. The lens is larger in diameter than the diameter of the optical fiber member.

13 Claims, 2 Drawing Sheets

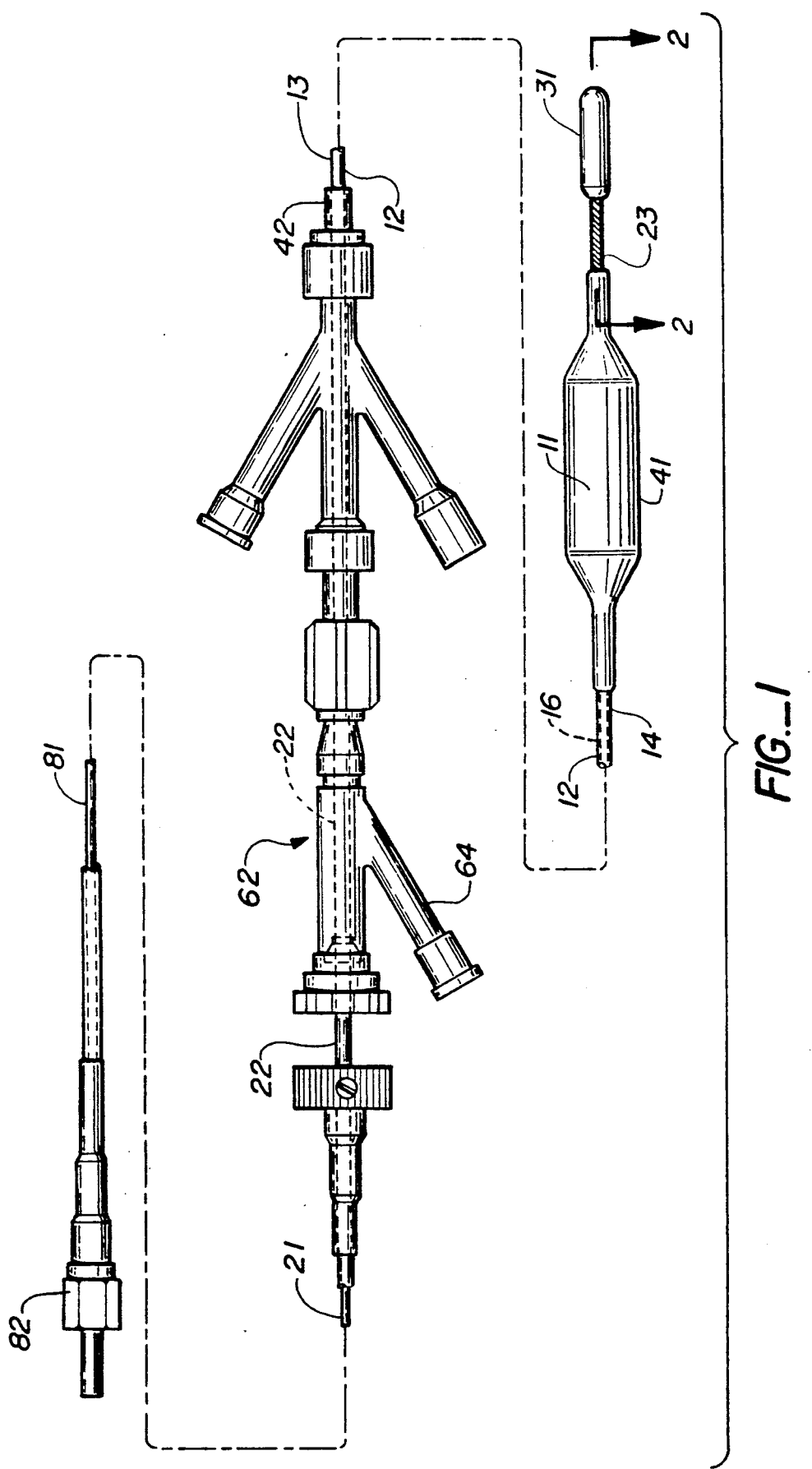
FIG._1

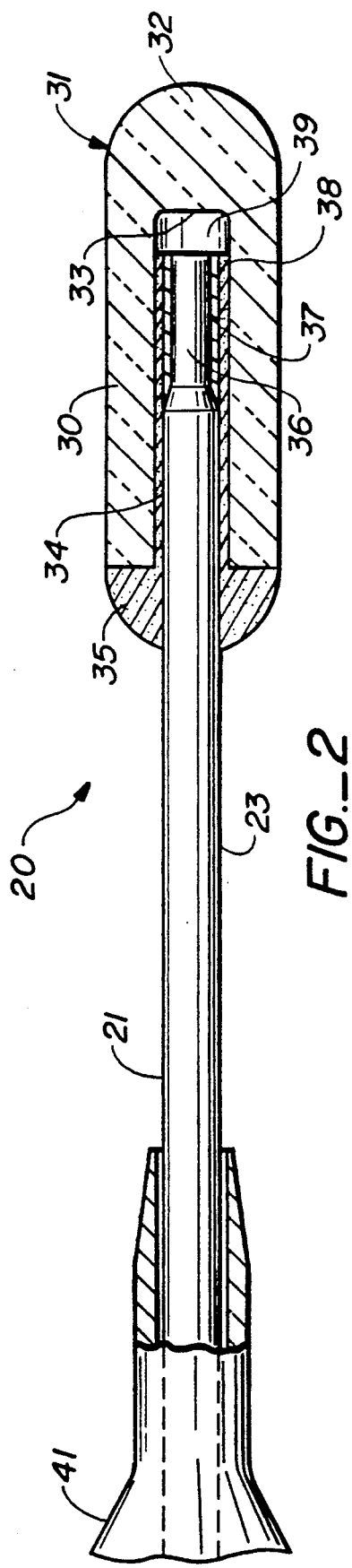
FIG._2
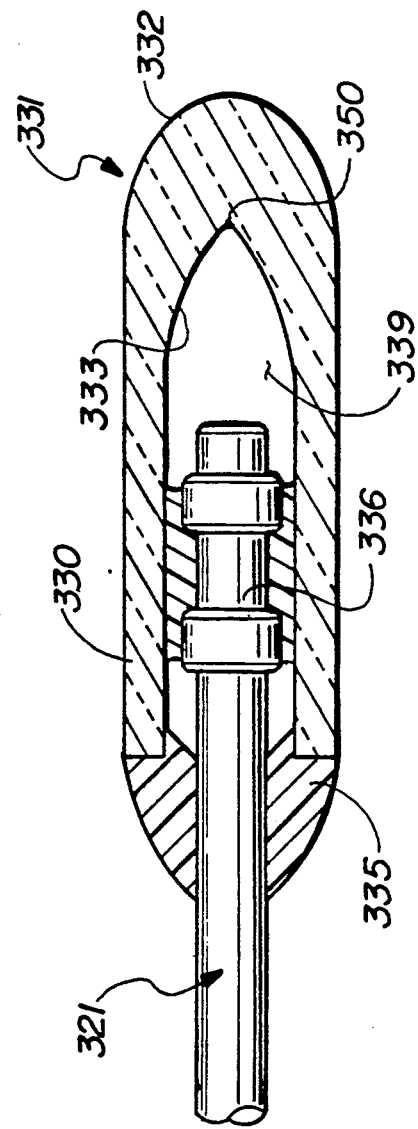
FIG._3

OPTICAL FIBER LASING APPARATUS LENS

FIELD OF THE INVENTION

This invention relates to optical fibers and more particularly to lenses for optical fiber devices having laser cutting capabilities.

BACKGROUND OF THE INVENTION

Laser optical fiber systems have been developed which incorporate an optical fiber assembly to conduct laser radiation from a remote location to a site at which a cutting procedure is to be performed. A lens is commonly attached to the optical fiber to focus and direct the laser radiation at the desired location.

In some applications, the laser cutting apparatus has been combined with an otherwise conventional balloon angioplasty catheter apparatus. The dilatation balloon catheter of the angioplasty apparatus could be advanced through the channel cut by the laser and then an angioplasty procedure could be performed in the conventional manner.

While such laser angioplasty systems were believed to hold great promise, they were later seen to have important limitations. Among these limitations was the inability to combine the needed flexibility of a small optical fiber with the ability to produce by ablation a large lumen. Later devices which utilized a ball tip were able to ablate large lumens if lasers were used that produced some lateral heating. This later heating can present risks to arterial walls and other tissue which is not desired to be ablated. Although pulsed lasers ablated without producing a large lateral thermal component, the lumen produced was smaller that the diameter of the ball lens.

Another limitation was that the apparatus was not structurally strong. This presents difficulties when the lumen produced is smaller than the diameter of the lens, because the lens has an enhanced risk of detachment upon retraction of the apparatus.

As other applications of laser surgery, especially in vivo procedures, have been developed, similar problems have surfaced. This is particularly true when the apparatus is to be manipulated from a remote location by means of a catheter. In such cases, the problem of confining the pattern of laser radiation to a predetermined region directly in front of the distal tip of the fiber has become very important and the subject of intense interest of designers.

These problems can be seen to be the result of the lenses which are presently used in fiber optical laser surgical systems. The typical distribution of radiation from prior art devices is Gaussian, i.e. is shaped like a bell curve. An ideal lens would confine all of the radiation to a region immediately forward of the catheter, and would distribute it evenly. Thus, the shape of such a distribution of radiation would be shaped like a square wave. In this manner the tissue directly in front of the lens would be cut and the device readily advanced.

In addition, the radiation ideally should be directed forward in a pattern as wide as the lens itself, in order to properly clear a path for the advancing apparatus. If this is not done, the advancing apparatus can trap flaps of uncut tissue which act to dislodge, or otherwise disturb, the lens upon retraction of the apparatus from the body. The desired radiation pattern thus is one where radiation is directed forward uniformly over the width of the lens while having negligible radiation beyond such an area. Such a radiation pattern cannot be achieved with typical prior art optical fiber laser lenses.

There remains, therefore, a need for an optical fiber system that allows the accurate direction of laser radiation to a selected site and reduces the chance of damage to the patient from dislodging or disintegrating of the lens end of the optical fiber. It would also be beneficial if such a system were readily adaptable to catheter configurations that could be used for a variety of surgical and intravascular procedures.

Broadly, it is the object of the present invention to provide an improved laser optical fiber lens apparatus and method for creating such an apparatus.

It is a further object of the present invention to provide a laser optical fiber lens apparatus capable of producing radiation patterns of a desired shape.

It is a still further object of the present invention to provide a laser optical fiber lens apparatus capable of directing radiation approximately uniformly forward over an area the size of the lens, with minimal radiation directed beyond that area.

It is a yet further object of the present invention to provide a laser optical fiber apparatus with improved attachment of the lens to the optical fiber.

These and other objects of the present invention will be apparent to those skilled in the art from the following detailed description of the invention and the accompanying drawings.

SUMMARY OF THE INVENTION

The present invention comprises an optical fiber lasing apparatus. The lasing apparatus includes an optical fiber element having proximal and distal portions and a distal end. The optical fiber element is adapted to conduct laser radiation from the proximal portion to be emitted at the distal portion. The lasing apparatus also includes a lens secured to the distal end of the optical fiber. The lens has a first lens surface adjacent to and spaced from the distal end of the optical fiber positioned to receive laser radiation emitted from the distal end of the optical fiber. The lens also has an second lens surface, which is substantially convex, positioned to emit laser radiation from the lens. The first lens surface is shaped to provide a predetermined emission pattern from the second lens surface. The lens may also include a tubular sleeve coupled to the first lens surface. The tubular sleeve extends from the first lens surface in a direction optically opposite to that of the second lens surface. In the preferred embodiment of the present invention, the tubular sleeve may be positioned over the optical fiber to provide structural support and improved attachment for the lens.

The present invention also comprises a lens adapted to be secured to an end of an optical fiber. The lens includes an second lens surface which is substantially convex. The lens also includes a first lens surface optically opposite the second lens surface. The first lens surface is shaped to provide a predetermined emission of laser radiation incident on the first lens surface from the second lens surface. The lens also includes a tubular sleeve extending from the first lens surface in a direction optically opposite the second lens surface. The tubular sleeve is of a size for mating with a laser radiation emitting optical fiber.

The present invention also comprises a method of constructing a lens assembly for an optical fiber. The method includes forming a lens element having a substantially cylindrical outer surface which terminates in a substantially convex first end. It also includes forming a cavity in a second end opposed to the first end. The cavity is sized to receive an optical fiber. The method also includes bonding the distal end of an optical fiber in the cavity in an attitude substantially aligned with the axis of the cylindrical outer surface.

BRIEF DESCRIPTION OF THE DRAWINGS

FIG. 1 is a side elevational view of a balloon dilatation catheter with laser cutting capabilities incorporated in the present invention.

FIG. 2 is an enlarged cross-sectional view of the distal extremity of the catheter shown in FIG. 1.

FIG. 3 is a cross-section of a preferred embodiment of lens 31 of FIGS. 1 and 2.

DETAILED DESCRIPTION OF THE PREFERRED EMBODIMENT

In general, the optical fiber lasing apparatus according to the present invention includes an optical fiber having a lens spaced adjacent to the distal end of an optical fiber and secured thereto. In one embodiment the optical fiber is disposed within a catheter and an inflatable balloon is carried on the distal extremity of the catheter.

More particularly, as is shown in FIGS. 1 and 2 of the drawings, an intravenous catheter 11 includes an elongate flexible tubular member 12 having a proximal extremity 13 and a distal extremity 14. Tubular member 12 can be formed of a suitable material such as polyethylene tubing, and can be of various sizes depending on the size of the vessel that is desired to be negotiated with the catheter. Tubular member 12 is provided with a lumen 16 extending the length thereof.

The optical fiber lasing assembly 20 of the present invention is preferably adapted to extend through lumen 16 of catheter 11, and includes optical fiber 21 which can have a suitable diameter such as 0.012 inches and can have a suitable length such as approximately 400 cm. In order to give additional rigidity to optical fiber 21 and to enhance its pushability, a proximal portion of optical fiber 21 is disposed within a metallic tube 22 or hypo-tube formed of a suitable material such as stainless steel.

The manner in which the present invention provides its advantages may best understood with reference to FIG. 2. Optical fiber lasing assembly 20 includes a lens 31 which is secured to the distal extremity 23 of optical fiber 21 by adhesive, such as epoxy 35. Lens 31 consists of a tubular portion 30 and a lens tip 32 formed from a suitable material such as glass or silica tubing. The distal surface of lens tip 32 acts as an second lens surface. In the preferred embodiment the surface of lens tip 32 is convex, or substantially convex. A surface is substantially convex if it is a combination of surfaces such that the combined surface's shape roughly approximates a convex surface. Alternative embodiments of the present invention may utilize a planar lens tips 32. Lens 31 includes a first lens surface 33 which receives laser radiation emitted from the distal end 36 of optical fiber 21. Lens 31 also includes an inner tubular channel 34 which fits over distal end 36 and is preferably secured to distal end 36 with epoxy adhesive 38.

Lens 31 may be formed from a section of approximately 3 mm. of fused silica or glass tubing having an approximate outer diameter of 1.0 mm and an inner diameter slightly greater than about 0.016 inches. One end of the tubing can be heated by a flame of a low temperature, such as may be created with a fuel of hydrogen and an additive of a mixture of acetone and alcohol.

Lens 31 can, if desired, have a diameter which is larger than the inside diameter of tubular member 12, which is the diameter of lumen 16. This would make optical fiber lasing assembly 20 non-removable when combined with the catheter assembly.

Lens 31 is also sized to have a diameter substantially larger than the diameter of optical fiber 21 to which it is connected. In practice, it has been found that lens diameters of approximately 1.0–3.0 mm are effective in focusing the laser light on the area of stenosis located in front of the lens. These may be used to advantage in assisting the advance of the catheter through an area of stenosis which has been enlarged due to laser cutting. Furthermore, a lens 31 which is large in comparison to the diameter of an optical fiber 21 provides an optical characteristic which optimizes the forward projection of light energy for oblation of tissue. This results in a reduction in the probability of damaging the arterial wall.

Lens 31 is self guiding and greatly reduces possible perforation of the side wall of the vessel being negotiated. Optical fiber lasing assembly 20 with its lens 31 facilitates negotiation of tortuous vessels.

The presently preferred embodiment of lens 31 is illustrated in FIG. 3. In this embodiment first lens surface 333 is aspheric as shown, coming to a point at apex point 350. Lens tip 332 is substantially convex. The other features are analogous to those described for FIG. 2.

Returning to FIGS. 1 and 2, a tubular ferrule 37 with an open end may also be placed over distal end 36 of optical fiber 21 to protect and shield the distal end of optical fiber 21, and may be secured to optical fiber 21 by epoxy adhesive. Ferule 37 may be constructed of gold or another radiopaque material to allow the lens tip to be detected by fluoroscopy or similar diagnostic tracking technique. Ferrule 37 may, for example, have an outer diameter of about 0.016 inches and an inner diameter of about 0.0085 inches.

The space 39 between distal end 36 of optical fiber 21 and first lens surface 33 can be empty space, or may be filled with a variety of substances with varying indices of refraction. The space allows the laser radiation emitted from distal end 36 to spread before being received at first lens surface 33. This spreading of the radiation allows the larger lens 31 to receive laser radiation from a smaller distal end 36 while providing radiation over the entirety of the distal surface of lens tip 32.

In a preferred embodiment as illustrated in FIG. 1, an inflatable balloon 41 is carried by the distal extremity of the tubular member 12. Balloon 41, as shown, can be formed integrally with an elongate flexible tubular member 42 which extends coaxially of tubular member 12. Balloon 41 can also be formed as a separate element and bonded to tubular member 42.

The operation of the present invention may now be described in further detail. The proximal extremity 81 of optical fiber 21 is secured to a suitable connector such as a conventional male SMA connector 82. Laser radiation is introduced by a laser (not shown) connected to SMA connector 82. This causes an appropriate amount of energy to be directed down optical fiber 21 and into lens 31. The laser radiation emitted from second lens tip 32 causes ablation of the atheromatous tissue in the stenosis while at the same time minimizing adjacent thermal injury to the vessel.

During this procedure, the tissue being irradiated can be immersed in a suitable saline solution by introducing the saline solution into the side arm 64 of a two arm adapter 62. Alternatively, the laser irradiation may occur in the presence of blood in the region adjacent lens 31. This is the case because one advantage of the present invention is that the radiation pattern of lens 31, which is concentrated in the immediate distal area of lens 31 concentric with lens 31, does not have to be actively aimed. Therefore lens 31 may be placed in close contact with the stenosis which is to be removed. Thus, there is very little blood between lens 31 and the stenosis to be irradiated by laser radiation and absorb the energy emitted.

The optical fiber apparatus disclosed herein may be used apart from a balloon dilation catheter to cut away or form channels in other tissue, and may be guided into position by other means, such as a guiding catheter.

There has been disclosed herein a lens and an optical fiber lasing system and method for creation of same. Various modifications to the present invention will become apparent to those skilled in the art from the foregoing description and accompanying drawings. Accordingly, the present invention is to be limited solely by the scope of the following claims.

What is claimed is:

1. An optical fiber lasing apparatus, comprising:
    laser radiation generation means to emit laser radiation of sufficient energy output to lase a channel through a predetermined material;
    an optical fiber element having proximal and distal portions and a proximal and a distal end, said proximal end being optically coupled to said laser radiation generation means, said optical fiber element conducting said laser radiation emitted from said laser generation means from said proximal end to be emitted at said distal end; and
    a lens secured to said distal portion of said optical fiber element, said lens having a first lens surface adjacent to and spaced from said distal end of said optical fiber element and positioned to receive laser radiation emitted therefrom, and a second lens surface positioned to emit laser radiation from said lens, said second lens surface being substantially convex, said first lens surface and said second lens surface respectively defining rearward and forward directions for said lens, said first lens surface being shaped to provide a predetermined emission pattern from said second lens surface over a predetermined area forward of said lens, said laser radiation being substantially contained to said area and being emitted substantially uniformly over said area.

2. The apparatus of claim 1, wherein said lens further comprises a tubular sleeve, said tubular sleeve being mechanically coupled to said first lens surface and extending from said first lens surface over at least a portion of said distal portion of said optical fiber element.

3. The apparatus of claim 2, wherein said mechanical coupling comprises a fusion of said tubular sleeve and said first lens surface.

4. The apparatus of claim 1, including a flexible elongated tubular member having proximal and distal extremities and at least one lumen therethrough, said optical fiber element passing through said lumen, said flexible elongated tubular member having an inflatable balloon near the distal end of said flexible elongated tubular member for positioning and anchoring said flexible elongated tubular member.

5. The apparatus of claim 1, wherein said first lens surface is concave and said second lens surface is aspherical.

6. The apparatus of claim 1, wherein said first lens surface is concave and second lens surface is spherical.

7. The apparatus of claim 6, wherein said first lens surface is aspheric.

8. The apparatus of claim 1, wherein said first lens surface is substantially conically concave.

9. An optical fiber lasing apparatus, comprising:
    laser radiation generation means to emit laser radiation of sufficient energy output to lase a channel through a predetermined material;
    an optical fiber element having proximal and distal portions and a proximal and a distal end, said proximal end being optically coupled to said laser radiation generation means, said optical fiber element conducting said laser radiation emitted from said laser generation means from said proximal end to be emitted at said distal end; and
    a lens secured to said distal portion of said optical fiber element, said lens having a first lens surface adjacent to and spaced from said distal end of said optical fiber element and positioned to receive laser radiation emitted therefrom, and a second lens surface positioned to emit laser radiation from said lens, said second lens surface being substantially convex, said first lens surface being shaped to provide a predetermined emission pattern from said second lens surface; and
    a tubular ferrule element disposed over said distal end of said optical fiber element to protect said distal end of said optical fiber element and to space said first lens surface from said distal end of said optical fiber.

10. The apparatus of claim 9, wherein said tubular ferrule element comprises a radiopaque tube.

11. An optical fiber lasing apparatus, comprising:
    laser radiation generation means to emit laser radiation of sufficient energy output to lase a channel through a predetermined material;
    an optical fiber element having proximal and distal portions and a proximal and a distal end, said proximal end being optically coupled to said laser radiation generation means, said optical fiber element conducting said laser radiation emitted from said laser generation means from said proximal end to be emitted at said distal end; and
    a lens secured to said distal portion of said optical fiber element, said lens having a first lens surface adjacent to and spaced from said distal end of said optical fiber element and positioned to receive laser radiation emitted therefrom, and a second lens surface positioned to emit laser radiation from said lens, said second lens surface being substantially convex, said first lens surface and said second lens surface respectively defining rearward and forward directions for said lens, said first lens surface being shaped to provide a predetermined emission pattern from said second lens surface over a predetermined area forward of said lens, said laser radiation being substantially contained to said area and being emitted substantially uniformly over said area;

wherein the space between the distal end of said optical fiber element and said first lens surface is occupied by a substance of preselected optical transmission characteristics.

12. A method of constructing a lens assembly for an optical fiber comprising:

forming a lens element having a substantially cylindrical outer surface terminating in a substantially convex first end and a substantially cylindrical cavity in a second end opposed to said first end; a said cavity being sized to receive an optical fiber, said cavity being larger than the diameter of said optical fiber inserting the distal end of said optical fiber into said cavity in an attitude substantially aligned with the axis of said cylindrical outer surface;

providing a space between said distal end of said optical fiber and the end of said cavity, such that a predetermined emission pattern of radiation is emitted form said lens element when laser radiation is input into the proximal end of said optical fiber and such that radiation so emitted will spread before being received at the end of said cavity, said emission pattern being such that radiation is substantially contained to an area directly opposite said first end of said lens element and being emitted substantially uniformly over said area; and bonding the distal end of said optical fiber to said lens element.

13. The method of claim 12 further comprising filling said space between said distal end of said optical fiber and the end of said cavity with a substance of predetermined optical transmission characteristics chosen to optimize said predetermined pattern of radiation.

* * * * *